United States Patent
Wohlgemuth et al.

(10) Patent No.: US 9,546,154 B2
(45) Date of Patent: Jan. 17, 2017

(54) METHOD FOR PRODUCING DABIGATRAN ETEXILATE METHANSULPHONATE

(71) Applicant: Boehringer Ingelheim International GmbH, Ingelheim am Rhein (DE)

(72) Inventors: Michael Guenter Wohlgemuth, Ingelheim am Rhein (DE); Volker Brenk, Bingen am Rhein (DE); Ingo Heddesheimer, Odernheim (DE); Bernhard Schmitz, Mainz am Rhein (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/819,504

(22) Filed: Aug. 6, 2015

(65) Prior Publication Data

US 2016/0039791 A1     Feb. 11, 2016

(30) Foreign Application Priority Data

Aug. 7, 2014 (EP) .................................. 14180217

(51) Int. Cl.
| | | |
|---|---|---|
| C07D 401/12 | (2006.01) | |
| G01N 21/3577 | (2014.01) | |
| G01N 21/552 | (2014.01) | |
| G01N 21/85 | (2006.01) | |
| G01N 21/84 | (2006.01) | |

(52) U.S. Cl.
CPC ......... *C07D 401/12* (2013.01); *G01N 21/3577* (2013.01); *G01N 21/552* (2013.01); *G01N 21/8507* (2013.01); *G01N 2021/8416* (2013.01)

(58) Field of Classification Search
CPC .................................................. C07D 401/12
USPC ........................................................ 546/273
See application file for complete search history.

(56) References Cited

U.S. PATENT DOCUMENTS 6,522,408 B1    2/2003    Bruck

FOREIGN PATENT DOCUMENTS

| | | | |
|---|---|---|---|
| DE | 19805612 | | 2/2013 |
| WO | WO2012027543 | * | 3/2012 |
| WO | 2012044595 A1 | | 4/2012 |
| WO | 2012110593 A1 | | 8/2012 |

OTHER PUBLICATIONS

International Search Report and Written opinion, ISA/220 for PCT/EP2015068143, mailed Sep. 3, 3015.

* cited by examiner

*Primary Examiner* — Noble Jarrell
*Assistant Examiner* — Daniel Carcanague
(74) *Attorney, Agent, or Firm* — Michael P. Morris; Edward S. Lazer

(57) ABSTRACT

An improved method of preparing dabigatran etexilate mesylate (1-salt),

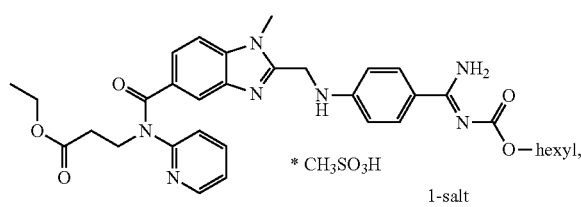

is described.

8 Claims, 2 Drawing Sheets

Schematic description of process monitoring

Figure 1: Schematic description of process monitoring
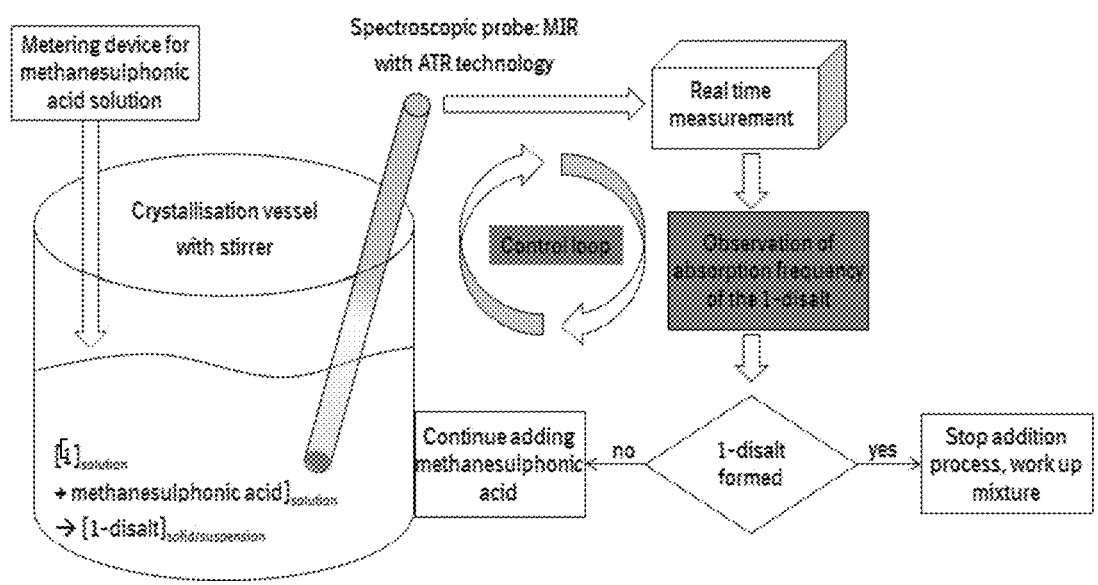

Figure 2: Spectrum diagram for illustrating the detection of 1-disalt
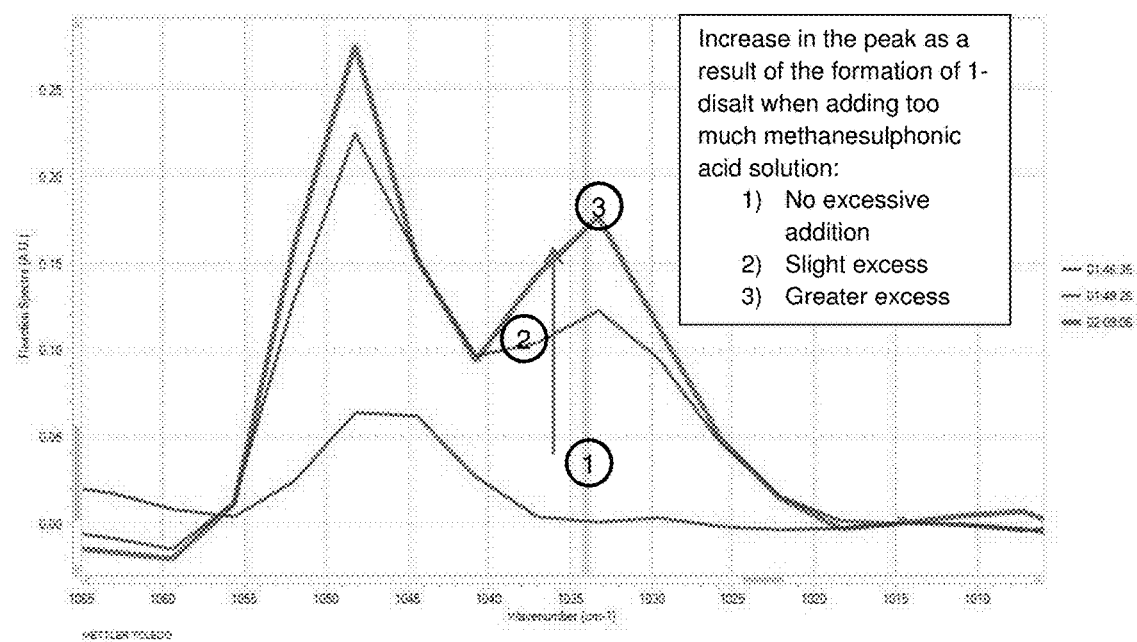

METHOD FOR PRODUCING DABIGATRAN ETEXILATE METHANSULPHONATE

Substituted (4-benzimidazol-2-ylmethylamino)-benzamidines, particularly dabigatran etexilate (CAS 593282-20-3; 1),

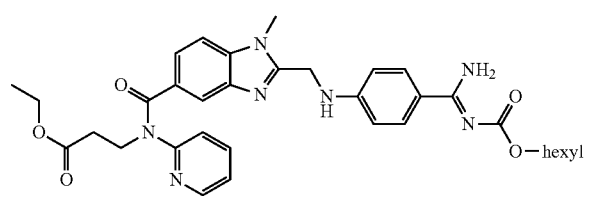

are already known from International Patent Application WO 98/37075 as active substances with a thrombin-inhibiting activity. The main indication sectors of the compound of formula 1 are the postoperative prophylaxis of deep vein thromboses and stroke prevention in patients with atrial fibrillation (SPAF). Dabigatran etexilate is used in pharmaceutical applications in the form of its methanesulphonic acid salt (hereinafter referred to as mesylate). Dabigatran etexilate mesylate was disclosed and described in WO 2003/074056.

In WO 98/37075 it is proposed to produce the substituted (4-benzimidazol-2-ylmethyl-amino)-benzamidines by reacting corresponding substituted (4-benzimidazol-2-ylmethyl-amino)-benzonitriles with ammonia. This process is onerous from the manufacturing point of view and results in a large quantity of acids that have to be disposed of (cf. WO 2007/071743, WO 2007/071742).

Another improved process for preparing the active substance dabigatran etexilate is proposed in WO2011/061080, in which, by switching to new starting materials and using phase transfer catalysis, a more efficient synthesis of dabigatran etexilate could be achieved.

The dabigatran etexilate mesylate salt (1-salt), preferably as a crystalline polymorph form I, is obtained according to WO 2003/074056 starting from dabigatran etexilate 1 by reacting with methanesulphonic acid (Scheme 1):

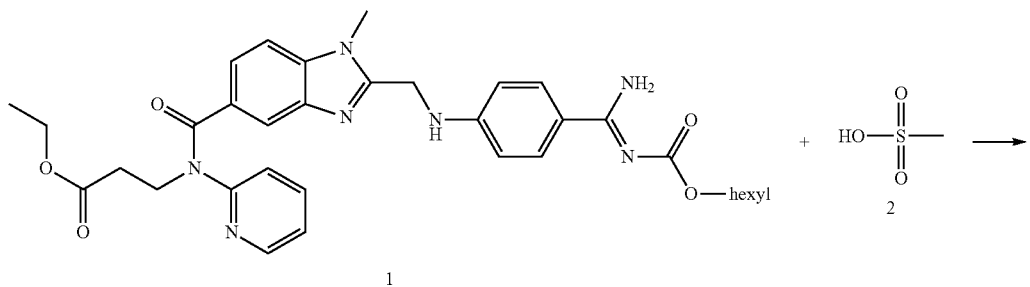

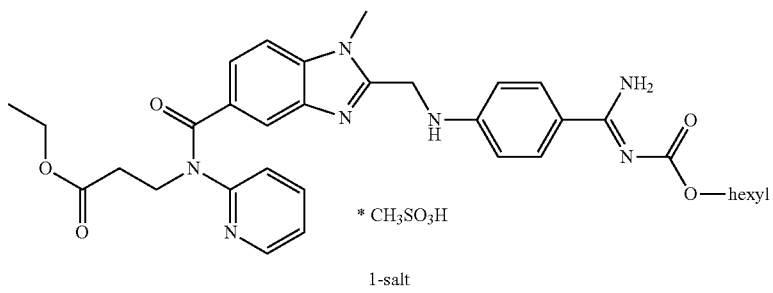

1-salt

The present invention is based on the problem of providing a technical method by which the dabigatran etexilate mesylate 1-salt is made available in an improved yield.

BRIEF DESCRIPTION OF THE DRAWINGS

The present invention will become apparent from the following description, examples and claims with reference to the Figures.

FIG. 1: Schematic description of process monitoring.

FIG. 2: Spectrum diagram for illustrating the detection of 1-disalt.

DETAILED DESCRIPTION OF THE INVENTION

Surprisingly, it has been found that dabigatran etexilate mesylate (1-salt) can be obtained in a particularly high yield and purity if the conversion of the reaction according to Scheme 1 is monitored and controlled by infrared spectroscopy (IR spectroscopy). In this monitoring of the reaction, the double salt of formula 1-disalt described in WO 2012/044595 is of particular importance.

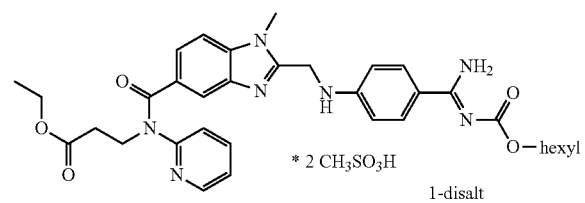

1-disalt

The invention thus relates to a method for preparing the compound of formula 1-salt

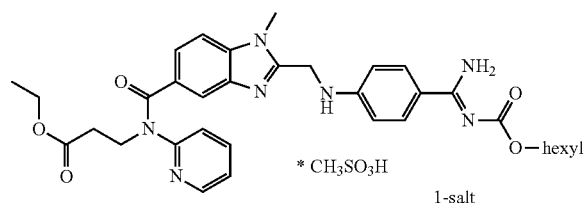

1-salt characterized in that dabigatran etexilate of formula 1

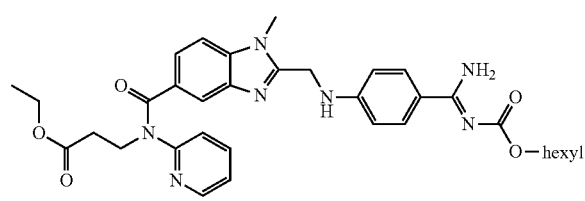

1 is combined with methanesulphonic acid 2

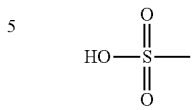

2 in a suitable solvent, until the formation of the compound of formula 1-disalt

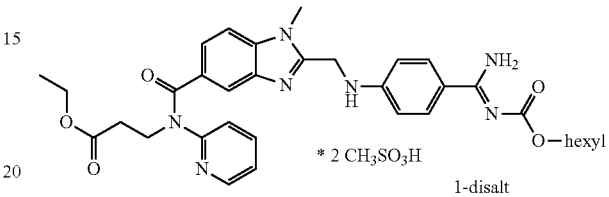

1-disalt can be detected by IR-spectroscopic process monitoring.

The process monitoring according to the invention can be used to ensure that quantitative reaction of compound 1 takes place. At the same time, increased formation of the unwanted compound 1-disalt is efficiently prevented.

The management of the reaction according to the invention minimises the need for purification of the product 1-salt, as the quantitative reaction of 1 to 1-salt is ensured even when the initial weights fluctuate.

In addition, the method according to the invention makes it possible to monitor the reaction precisely, even in the case of mixtures in which the starting materials 1 and 2 have different purities and consequently fluctuating contents, as a result of the manufacturing process.

The method according to the invention achieves without any additional input in the manufacture of the product a content of 1-salt in the range from 98 to 100%, preferably in the range from 99.50 to 99.98%, for example 99.93%. The method according to the invention thus achieves an increase in yield of 1 to 10%, for example 3%, compared with the conventional method mentioned previously.

The compound 1-salt is prepared by the following method. The dabigatran etexilate 1 used according to the invention may be obtained as described in the prior art (cf. WO 98/37075, Example 113).

According to the invention, 1 is dissolved in a suitable solvent and put in the reaction. Organic, weakly polar solvents may be used as the solvent. Preferably, according to the invention, the solvent is selected from among ethyl acetate, methyl acetate, methylethylketone and acetone, of which ethyl acetate and acetone are preferred according to the invention. Particularly preferably, the compound of formula 1 is placed in acetone and dissolved.

According to the invention, the methanesulphonic acid 2 is preferably also dissolved in one of the above-mentioned solvents before being added to the solution of compound 1. Particularly preferably, the same solvent in which 1 has already been dissolved may be used.

Preferably, the methanesulphonic acid 2 is added with stirring and in batches.

Theoretically, stoichiometric amounts of the acid 2 are required for the total reaction of 1 to form 1-salt. If for example one mole of dabigatran etexilate 1 is to be reacted to form one mole of dabigatran etexilate mesylate 1-salt, one mole of methanesulphonic acid 2 is required. The methanesulphonic acid 2 preferably dissolved in one of the above-mentioned solvents is preferably added batchwise.

A particularly preferred procedure comprises a continuous first addition of over 50% of the total amount (corresponding to 50 mol % of the dissolved methanesulphonic acid) within 10 minutes up to about 2 hours, preferably within 15 to 90 minutes, particularly preferably within 20 to 40 minutes. Preferably during this first addition, more than 60 mol %, preferably more than 70 mol %, preferably more than 80 mol %, preferably between 94 and 96 mol % of the dissolved methanesulphonic acid 2 are metered in continuously. Preferably, the maximum addition of 2 is not more than 99 mol % of the total amount of 2 theoretically required for the complete reaction of 1 into 1-salt.

In the second metering stage, the remaining amount of 2 is added either continuously over a period of 5 to 60 minutes, preferably within 10 to 40 minutes, preferably within 15 to 25 minutes, or batchwise in amounts of 0.1 to 1 mol % of the total quantity of 2. Particularly preferably, the addition in the second metering stage is carried out batchwise.

During the second metering stage the IR-spectroscopic reaction monitoring is carried out.

As illustrated in FIG. 1, a measuring probe with ATR technology (Attenuated Total Reflection) for measuring IR spectra is installed in an immersion tube and thus penetrates into the liquid medium which is to be examined in a reaction vessel. The probe is connected to an IR-spectrometer and computer for producing and evaluating the absorption spectra. The spectra, analyzed in real time, deliver a signal via the computer to a control circuit indicating the absence, formation or existence of the disalt (1-disalt). If 1-disalt is present, the addition of methanesulphonic acid 2 is automatically stopped by means of a process management system.

The measuring principle according to the invention is based on the detection of typical spectral resonances of the 1-disalt. The following spectral bands may be emphasized, for example (measured in acetone solution using the ReactIR 45m; measuring equipment from Mettler Toledo):

1047 $cm^{-1}$ (absorption peak: 1-salt and 1-disalt/R—$NH_3^+$),

1034 $cm^{-1}$ (absorption peak: 1-disalt/R—$NH_2^+$—R'

The IR spectrum of compound 1-disalt determined accordingly is shown in FIG. 2.

The IR-spectroscopic reaction monitoring is carried out with a measuring probe which dips into the reaction medium. This can be achieved by various methods. For example, the IR probe may be arranged so that it dips into the reaction medium as the result of a stirring operation that has been carried out. Alternatively, it may also be installed in a bypass loop through which the reaction medium is conveyed out of the reaction vessel, past the IR probe and back into the reaction vessel by means of a pump. Other possible embodiments comprise, for example, the introduction of the IR probe through a base valve or the like. In any case the configuration must be such that the probe extends into the reaction medium.

The probe constitutes ATR (attenuated total reflection) technology in which infrared light is introduced into a diamond wafer from one side. In the diamond, the light travels onwards by being reflected multiple times from one internal side of the disc to the other side until it has passed through the diamond and re-emerges for analysis in the spectrometer. The diamond wafer comes into contact with the reaction medium on one side. At this point of contact, an interaction occurs between the IR light and the reaction medium, in which the IR light is attenuated by light absorption. The attenuation takes place in those wavelength ranges that are typical for the molecules contained in the reaction medium.

An embodiment of an ATR probe is described for example in "Internal Reflection and ATR Spectroscopy (Chemical Analysis: A Series of Monographs on Analytical Chemistry and Its Applications)", Milan Milosevic, Wiley, 2012 (commercially available).

An IR spectrum of the reaction mixture is taken at regular intervals using the probe described above by means of an FT-MIR (Fourier-Transformation Middle Infrared Resonance) spectrometer. The spectra are taken at regular time intervals. The shorter the time intervals between the individual measurements, the more accurately the progress of the reaction can be observed.

In a preferred embodiment, at least 1, preferably 2, more preferably between 3 and 10, particularly preferably between 4 and 8 measurements are carried out per minute.

Immediately after each automatic measurement and Fourier transformation the absorption is determined in the wavelength range of 1045 $cm^{-1}$ to 1015 $cm^{-1}$, particularly preferably at 1034 $cm^{-1}$. As is known, small deviations in the absorption ranges may occur, depending on the design, mode of operation and condition of the spectrometer and the probe.

The signal intensity of the absorption measured is standardized by subtracting the signal intensity of the baseline at one point or a number of points in the ranges from 798 to 838 $cm^{-1}$, 987-1027 $cm^{-1}$, 1107-1147 $cm^{-1}$, 1133-1173 $cm^{-1}$ and/or 1250-1290 $cm^{-1}$, for example at 1015 $cm^{-1}$, from a signal intensity or a number of signal intensities in the range from 1015-1045 $cm^{-1}$, preferably from 1018-1040 $cm^{-1}$, more preferably from 1032-1038 $cm^{-1}$, particularly preferably 1035 $cm^{-1}$. If a number of points along the baseline are used for the baseline standardisation or signal intensities for the 1-disalt signal, this also refers to signal areas within the ranges specified above.

As soon as an increase in the standardized signal intensity at 1034 $cm^{-1}$ is detected in one of the measurements carried out, this indicates the formation of the compound 1-disalt. As a result, the metered addition of the remaining methanesulphonic acid 2 is stopped.

The following items of equipment were used to collect the data provided above:

FT-MIR (Fourier Transformation Middle Infrared) Spectrometer ReactIR™ 45 m with ATR (Attenuated total reflectance) inline measuring probe (AgX-fibre probe 2 m long (D-Sub, 30 cm insertion depth)), Software iCIR™, manufactured by Mettler Toledo.

FT-MIR Spectrometer MonARC™ including an ATR inline measuring probe, Software iCIR™, manufactured by Mettler Toledo.

Enamelled agitator vessel 6.000 L, manufactured by Pfaudler.

Laboratory reactor LabMax® 1 L, manufactured by Mettler Toledo.

The threshold for switching off the equipment is dependent on the measuring sensitivity of the spectrometer used. Thus the baseline may be situated at different values of IR absorption. Basically, the detection of the 1-disalt occurs when the value [baseline level at 1035 $cm^{-1}$ minus baseline level at 1018 $cm^{-1}$] increases significantly.

This recognition or detection limit may be defined according to the generally known rules of statistics (e.g. Handbuch der Validierung in der Analytik (German Edition), Stavros Kromidas, p. 195, Wiley, 1st Edition, 2000). A signal is thus deemed to be detected when its value is at least 3 times greater than the signal noise or the measurement error.

For example, the switch-off value may be determined as a function of the signal intensity of the background noise according to the following formula:

Switch-off value≥$n$*background noise signal+(baseline level at 1034 cm$^{-1}$–baseline level at 1018 cm$^{-1}$ after the end of the 95 mol % addition and before the pulsed metering).

n may denote the value 3 to 50, preferably 3.

The present invention further relates to the use of the compound of formula 1-disalt as an indicator for the IR-spectroscopic monitoring of the reaction.

EXPERIMENTAL SECTION

In the following section, the present invention is explained in more detail by reference to specific embodiments by way of example. These embodiments serve purely to illustrate the method according to the invention and are not intended to limit the invention to the scope of the embodiments themselves.

In the synthesis examples that follow, the following items of equipment were used:

FT-MIR spectrometer MonARC™ with an ATR inline measuring probe (AgX-fibre probe 2 m long (D-Sub, 30 cm insertion depth)), Software iCIR™, manufactured by Mettler Toledo.

FT-MIR spectrometer ReactIR™45m with ATR inline measuring probe (AgX-fibre probe 2 m long (D-Sub, 30 cm insertion depth)), manufactured by Mettler Toledo.

Laboratory reactor LabMax® 1 L, manufactured by Mettler Toledo.

Compound 1-salt is prepared using the following method:

A reactor with heating means and a metering device (e.g. a dropping funnel) is fitted with an ATR immersion probe. The ATR immersion probe is connected to a spectrometer for measuring the absorption in the middle infrared range.

The probe is installed so that the tip of the probe comprising the optical measuring device is wetted completely by the dabigatran etexilate base reaction mixture during stirring.

A solution of 20 g dabigatran etexilate 1 in 189.7 g of acetone is stirred at 30 to 36° C. (preferably 33° C.) in the above-mentioned reactor and inoculated with 20 mg of dabigatran etexilate mesylate 1-salt.

Then 95% of a solution of 3.1 g of methanesulphonic acid (>99%) in 31.2 g acetone is metered in at 33° C. over a period of at least 35 min. This corresponds to 95 mol % of the methanesulphonate solution which is required for total crystallisation of the amount of dabigatran etexilate present in order to form the 1-salt and which is to be understood, within the scope of the invention, as mol % of the methanesulphonic acid solution, based on dabigatran etexilate, This metered addition may be carried out both batchwise and continuously. During the addition, the observation of the 1-disalt IR absorption at 1034 cm$^{-1}$ is begun after the addition of 20 mol %, preferably 50 mol %, for example 80 mol %.

After 95 mol % have been added, the addition is interrupted and the following 5 mol % are added in several batches, for example of the order of 0.5 mol %.

After the addition of each batch, the "signal to noise" value, standardized to the baseline height at 1015 cm$^{-1}$, is read off from the signal height of the 1-disalt absorption at 1035 cm$^{-1}$. If this value meets the criterion of being greater than three times the noise signal, the compound 1-disalt has formed and no more batches of methanesulphonic acid solution should be added.

If, after the addition of the methanesulphonic acid solution, no signal>than 3× the signal noise at the wavelength specified is observed, the batchwise addition is continued with more solution of methanesulphonic acid according to the recipe stated previously, until a detectable 1-disalt signal is received. The background to this might be a slightly higher concentration or molar amount of dabigatran etexilate or too low a concentration of methanesulphonic acid in the solution in question. Both may be caused by fluctuations in weighing or variations in quality.

After this reaction to form the 1-salt Polymorph Form 1 is isolated as a solid, after centrifugation and drying.

The invention claimed is:

1. A method for preparing the compound of the formula 1-salt

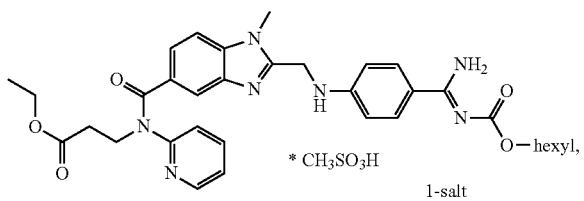

characterized in that dabigatran etexilate of formula 1

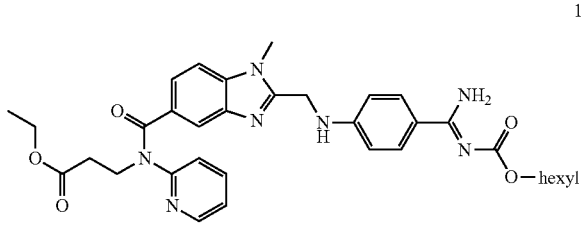

is combined with methanesulphonic acid 2

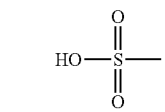

in a suitable solvent, wherein IR-spectroscopic monitoring of the combination process is carried out by means of an IR probe immersed in the reaction medium and wherein up to 99 mol% methanesulfonic acid is added to the dabigitran etexilate in a first addition and the remaining amount of methanesulfonic acid is added continuously or batchwise in a second stage until the formation of the compound of formula 1-disalt

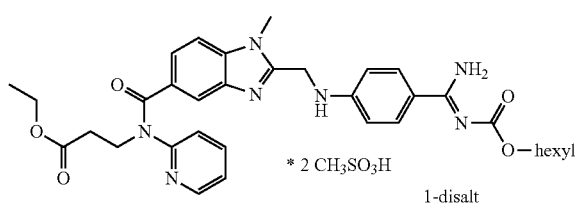

1-disalt is detected by the IR-spectroscopic monitoring of the process and the addition of methanesulfonic acid is stopped.

2. The method according to claim 1, wherein the occurrence of one or more spectral bands between 1030 and 1050 cm$^{-1}$ acts as an indicator for the formation of the compound of formula 1-disalt for IR-spectroscopic monitoring of the reaction.

3. The method according to claim 1, wherein the occurrence of two spectral bands between 1030 and 1050 cm$^{-1}$ serves as an indicator for the formation of the compound of formula 1-disalt for IR-spectroscopic monitoring of the reaction.

4. The method according to claim 1, wherein the occurrence of a spectral band between 1033 and 1035 and of a spectral band between 1046 and 1048 cm$^{-1}$ serves as an indicator for the formation of the compound of formula 1-disalt for IR-spectroscopic monitoring of the reaction.

5. The method according to claim 1, wherein the IR-spectroscopic monitoring of the process is carried out by means of a bypass loop through which the reaction medium is conveyed out of the reaction vessel, past the probe and back into the reaction vessel, by means of a pump.

6. The method according to claim 1, wherein an IR probe with ATR (attenuated total reflection) technology is used for the IR-spectroscopic monitoring of the process.

7. The method according to claim 1, wherein 3 to 10 measurements per minute are carried out for the IR-spectroscopic monitoring of the process.

8. The method according to claim 1, wherein up to 95% of the methanesulphonic acid is added in the first addition and the following 5 mol% is added in batches in the second stage.

* * * * *